(12) United States Patent
Xu et al.

(10) Patent No.: US 11,058,613 B2
(45) Date of Patent: *Jul. 13, 2021

(54) SUNCARE COMPOSITIONS

(71) Applicants: Rohm and Haas Company, Collegeville, PA (US); Dow Global Technologies LLC, Midland, MI (US)

(72) Inventors: Wenjun Xu, Phoenixville, PA (US); Fanwen Zeng, Audubon, PA (US); Benjamin Yezer, Conshohocken, PA (US); Liang Chen, Sewickley, PA (US); Dale C. Schmidt, South Jordan, UT (US); Inna Shulman, Langhorne, PA (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/634,320

(22) PCT Filed: Jun. 28, 2018

(86) PCT No.: PCT/US2018/039984
§ 371 (c)(1),
(2) Date: Jan. 27, 2020

(87) PCT Pub. No.: WO2019/022914
PCT Pub. Date: Jan. 31, 2019

(65) Prior Publication Data
US 2020/0268619 A1     Aug. 27, 2020

Related U.S. Application Data

(60) Provisional application No. 62/538,044, filed on Jul. 28, 2017.

(51) Int. Cl.
| | | |
|---|---|---|
| *A61K 8/02* | (2006.01) | |
| *A61K 8/34* | (2006.01) | |
| *A61K 8/81* | (2006.01) | |
| *A61K 8/86* | (2006.01) | |
| *A61K 8/89* | (2006.01) | |
| *A61Q 17/04* | (2006.01) | |

(52) U.S. Cl.
CPC ............ *A61K 8/0279* (2013.01); *A61K 8/34* (2013.01); *A61K 8/8117* (2013.01); *A61K 8/8147* (2013.01); *A61K 8/8152* (2013.01); *A61K 8/86* (2013.01); *A61K 8/89* (2013.01); *A61Q 17/04* (2013.01); *A61K 2800/412* (2013.01); *A61K 2800/413* (2013.01); *A61K 2800/5422* (2013.01); *A61K 2800/5424* (2013.01); *A61K 2800/5922* (2013.01); *A61K 2800/654* (2013.01)

(58) Field of Classification Search
CPC ...... A61K 8/0279; A61K 8/34; A61K 8/8117; A61K 8/8147; A61K 8/8152; A61K 8/86; A61K 8/89; A61K 2800/412; A61K 2800/413; A61K 2800/5422; A61K 2800/5424; A61K 2800/5922; A61K 2800/654; A61K 2800/54; A61K 2800/624; A61K 8/0241; A61Q 17/04
See application file for complete search history.

(56) References Cited

U.S. PATENT DOCUMENTS

| | | |
|---|---|---|
| 4,427,836 A | 1/1984 | Kowalski et al. |
| 5,663,213 A | 9/1997 | Jones et al. |
| 5,849,273 A * | 12/1998 | Bonda ............ A61K 8/35 424/59 |
| 6,384,104 B1 | 5/2002 | Chang et al. |
| 9,051,341 B2 | 6/2015 | Palmer, Jr. |
| 9,102,775 B2 | 8/2015 | Bardman et al. |
| 9,255,206 B2 | 2/2016 | Palmer, Jr. et al. |
| 2009/0035234 A1 | 2/2009 | Cunningham et al. |
| 2014/0017186 A1 | 1/2014 | Wang |

FOREIGN PATENT DOCUMENTS

| | | |
|---|---|---|
| AU | 2381099 | 6/1999 |
| EP | 1092421 A2 | 4/2001 |
| WO | 2010048124 A2 | 4/2010 |
| WO | 2017058713 | 4/2017 |

OTHER PUBLICATIONS

"Reactive Surfactants for Emulsion Polymerization," Technical Bulletin, E-Sperse RS-Series, Ethox Chemicals, LLC.

* cited by examiner

*Primary Examiner* — Snigdha Maewall
(74) *Attorney, Agent, or Firm* — Thomas S. Deibert

(57) ABSTRACT

A suncare formulation comprising: a dermatologically acceptable organic carrier; a UV radiation absorbing agent; and an SPF booster; wherein the SPF booster comprises a multistage polymeric particle having a core comprising polymerized units of a monoethylenically unsaturated carboxylic acid core monomer and a non-ionic ethylenically unsaturated core monomer; an inner shell comprising polymerized units of a non-ionic ethylenically unsaturated inner shell monomer; a monoethylenically unsaturated carboxylic acid inner shell monomer and an aliphatic inner shell monomer; an outer shell comprising polymerized units of a non-ionic ethylenically unsaturated outer shell monomer; an aliphatic outer shell monomer; a monoethylenically unsaturated non-carboxylic acid outer shell monomer and an ethylenically unsaturated surfactant outer shell monomer; wherein the core, when dry, contains a void; wherein the multistage polymeric particle has an average particle size, when dry, of 50 to 1,000 nm.

10 Claims, No Drawings

SUNCARE COMPOSITIONS

The present invention relates to a suncare formulation. In particular, the present invention relates to a suncare formulation, comprising: a dermatologically acceptable organic carrier; a UV radiation absorbing agent; and an SPF booster; wherein the SPF booster comprises a multistage polymeric particle having a core comprising polymerized units of a monoethylenically unsaturated carboxylic acid core monomer and a non-ionic ethylenically unsaturated core monomer; an inner shell comprising polymerized units of a non-ionic ethylenically unsaturated inner shell monomer; a monoethylenically unsaturated carboxylic acid inner shell monomer and an aliphatic inner shell monomer; an outer shell comprising polymerized units of a non-ionic ethylenically unsaturated outer shell monomer; an aliphatic outer shell monomer; a monoethylenically unsaturated non-carboxylic acid outer shell monomer and an ethylenically unsaturated surfactant outer shell monomer; wherein the core, when dry, contains a void; wherein the multistage polymeric particle has an average particle size, when dry, of 50 to 1,000 nm.

The damaging effects of sunlight on human skin are well documented. Six percent of the solar energy reaching the Earth's surface is ultraviolet (UV) radiation having a wavelength of 290 to 400 nm. This radiation is divided into two components: (i) low energy UVA radiation having a wavelength of 320 to 400 nm and (ii) high energy UVB radiation having a wavelength of 290 to 320 nm. While the UV portion of solar energy is relatively small, it induces nearly 99% of all the side effects from sunlight exposure. High energy UVB radiation, for example, is responsible for producing sunburn, appearance of skin aging and skin cancer. Low energy UVA radiation, for example, is responsible for inducing direct tanning and erythema (abnormal redness) of the skin and contributes to the appearance of skin aging.

By avoiding direct exposure to sunlight, individuals can avoid the serious effects caused by exposure to UV radiation. However, because of the nature of their work, it is challenging for some people to avoid such exposure. In addition, some people voluntarily expose their skin to the sun, e.g., to tan. Therefore, protection against the harmful effects of the sun is important.

Protection from the harmful effects of UV radiation exposure is available in the form of both topically applied formulations containing at least one physical UV blocker, or at least one chemical UV absorber, or combinations thereof. Physical blockers include active ingredients such as, titanium dioxide, zinc oxide and red petrolatum. Chemical absorbers include active ingredients, such as, paraaminobenzoic acid (more commonly known as PABA), which are generally transparent when applied and act by absorbing UV radiation, offering selective protection against certain UV wave bands, depending on the absorption spectrum of the active ingredient in the formulation.

The effectiveness of a given sunscreen formulation is assessed by how well it protects the skin in terms of a Sun Protection Factor (SPF) which is defined as the ratio of the amount of energy required to produce a minimal erythema on sunscreen protected skin to the amount of energy required to produce the same level of erythema on unprotected skin.

A number of the chemical absorbers and physical blockers, herein after referred to as "UV radiation absorbing agents," typically used in sunscreen formulations reportedly have adverse toxicological effects and negative sensory effects, which discourage people from using sunscreens. Therefore, it is desirable to reduce the level of UV radiation absorbing agents present in sunscreen formulations without reducing the SPF protection. Accordingly, a variety of SPF boosters have been developed for use in water based sunscreen formulations to reduce the level of UV radiation absorbing agents without a reduction in the SPF protection provided.

To that end, an approach to improving UV radiation absorption of a composition containing at least one UV radiation absorbing agent through the incorporation of a voided latex particle is disclosed in U.S. Pat. No. 5,663,213 to Jones et al. Jones et al. disclose a method for improving UV radiation absorption of a composition, comprising: adding to said composition from about 0.1 weight percent to about 50 weight percent of latex particles, based on total weight non-volatiles, wherein the composition comprises at least one UV radiation absorbing agent, wherein the latex particles contain a void and have a particle size of from about 100 nm to about 380 nm, and wherein the latex particles are added to increase the UV radiation absorption of the composition.

Notwithstanding, alcohol-based sunscreen products (e.g., sprays) account for up to 50% of the market. High alcohol content (e.g., >60 wt % ethanol) sunscreens are a popular format for which many conventional SPF booster offerings are unsuited.

To achiever desired SPF ratings in organic carrier based (sprayable) suncare formulations, conventional formulations incorporate high levels of expensive UV absorbing agents. While increasing the cost of the formulations, the incorporation of high levels of UV absorbing agents also negatively impair the aesthetics of these conventional formulations often imparting a tacky or gritting sensation on the skin.

Accordingly, there remains a need for new alcohol based suncare formulations that provide an effective SPF rating while reducing the necessary incorporation level of UV absorbing agents and enhancing the aesthetics of the formulation during use.

The present invention provides a suncare formulation, comprising: a dermatologically acceptable organic carrier; a UV radiation absorbing agent; an SPF booster, wherein the SPF booster comprises a multistage polymeric particle, comprising: (i) a core, wherein the core comprises, as polymerized units, 20 to 60 wt %, based on weight of the core, of a monoethylenically unsaturated carboxylic acid core monomer; and 40 to 80 wt %, based on weight of the core, of a non-ionic ethylenically unsaturated core monomer; (ii) an inner shell, wherein the inner shell comprises, as polymerized units, 90 to 99.9 wt %, based on weight of the inner shell, of a non-ionic ethylenically unsaturated inner shell monomer; 0.01 to 9.95 wt %, based on weight of the inner shell, a monoethylenically unsaturated carboxylic acid inner shell monomer; and 0.05 to 9.99 wt %, based on weight of the inner shell, of an aliphatic inner shell monomer selected from the group consisting of allyl acrylate, allyl methacrylate and mixtures thereof; (iii) an outer shell, wherein the outer shell comprises, as polymerized units, 10 to 45 wt %, based on weight of the outer shell, of a non-ionic ethylenically unsaturated outer shell monomer; 50 to 88.9 wt %, based on weight of the outer shell, of an aliphatic outer shell monomer selected from the group consisting of allyl acrylate, allyl methacrylate and mixtures thereof; 0.1 to 10 wt %, based on weight of the outer shell, of a monoethylenically unsaturated non-carboxylic acid outer shell monomer; and, 1 to 25 wt %, based on weight of the outer shell, of an ethylenically unsaturated surfactant outer shell monomer; wherein the core, when dry, contains at least one void;

and wherein the multistage polymeric particle has an average particle size, when dry, of 50 to 1,000 nm.

The present invention provides a suncare formulation, comprising: a dermatologically acceptable organic carrier; a film forming agent; a UV radiation absorbing agent; an SPF booster, wherein the SPF booster comprises a multistage polymeric particle, comprising: (i) a core, wherein the core comprises, as polymerized units, 20 to 60 wt %, based on weight of the core, of a monoethylenically unsaturated carboxylic acid core monomer; and 40 to 80 wt %, based on weight of the core, of a non-ionic ethylenically unsaturated core monomer; (ii) an inner shell, wherein the inner shell comprises, as polymerized units, 90 to 99.9 wt %, based on weight of the inner shell, of a non-ionic ethylenically unsaturated inner shell monomer; 0.01 to 9.95 wt %, based on weight of the inner shell, a monoethylenically unsaturated carboxylic acid inner shell monomer; and 0.05 to 9.99 wt %, based on weight of the inner shell, of an aliphatic inner shell monomer selected from the group consisting of allyl acrylate, allyl methacrylate and mixtures thereof; (iii) an outer shell, wherein the outer shell comprises, as polymerized units, 10 to 45 wt %, based on weight of the outer shell, of a non-ionic ethylenically unsaturated outer shell monomer; 50 to 88.9 wt %, based on weight of the outer shell, of an aliphatic outer shell monomer selected from the group consisting of allyl acrylate, allyl methacrylate and mixtures thereof; 0.1 to 10 wt %, based on weight of the outer shell, of a monoethylenically unsaturated non-carboxylic acid outer shell monomer; and, 1 to 25 wt %, based on weight of the outer shell, of an ethylenically unsaturated surfactant outer shell monomer; wherein the core, when dry, contains at least one void; and wherein the multistage polymeric particle has an average particle size, when dry, of 50 to 1,000 nm.

The present invention provides a suncare formulation, comprising: a dermatologically acceptable organic carrier; a UV radiation absorbing agent; an SPF booster, wherein the SPF booster comprises a multistage polymeric particle, comprising: (i) a core, wherein the core comprises, as polymerized units, 20 to 60 wt %, based on weight of the core, of a monoethylenically unsaturated carboxylic acid core monomer; and 40 to 80 wt %, based on weight of the core, of a non-ionic ethylenically unsaturated core monomer; (ii) an inner shell, wherein the inner shell comprises, as polymerized units, 90 to 99.9 wt %, based on weight of the inner shell, of a non-ionic ethylenically unsaturated inner shell monomer; 0.01 to 9.95 wt %, based on weight of the inner shell, a monoethylenically unsaturated carboxylic acid inner shell monomer; and 0.05 to 9.99 wt %, based on weight of the inner shell, of an aliphatic inner shell monomer selected from the group consisting of allyl acrylate, allyl methacrylate and mixtures thereof; (iii) an outer shell, wherein the outer shell comprises, as polymerized units, 10 to 45 wt %, based on weight of the outer shell, of a non-ionic ethylenically unsaturated outer shell monomer; 50 to 88.9 wt %, based on weight of the outer shell, of an aliphatic outer shell monomer selected from the group consisting of allyl acrylate, allyl methacrylate and mixtures thereof; 0.1 to 10 wt %, based on weight of the outer shell, of a monoethylenically unsaturated non-carboxylic acid outer shell monomer; and, 1 to 25 wt %, based on weight of the outer shell, of an ethylenically unsaturated surfactant outer shell monomer; wherein the core, when dry, contains at least one void; wherein the multistage polymeric particle has an average particle size, when dry, of 50 to 1,000 nm; and wherein the multistage polymeric particle contains less than 0.001 wt %, based on weight of the multistage polymeric particle, of polymerized units of styrene monomer in the backbone chain of the core, the inner shell and the outer shell combined.

The present invention provides a suncare formulation, comprising: a dermatologically acceptable organic carrier; a UV radiation absorbing agent; an SPF booster, wherein the SPF booster comprises a multistage polymeric particle, comprising: (i) a core, wherein the core comprises, as polymerized units, 20 to 60 wt %, based on weight of the core, of a monoethylenically unsaturated carboxylic acid core monomer; and 40 to 80 wt %, based on weight of the core, of a non-ionic ethylenically unsaturated core monomer; (ii) an inner shell, wherein the inner shell comprises: a first inner shell, wherein the first inner shell comprises, as polymerized units, 90 to 99.9 wt %, based on weight of the first inner shell, of a non-ionic ethylenically unsaturated first inner shell monomer; and 0.1 to 10 wt %, based on weight of the first inner shell, a monoethylenically unsaturated carboxylic acid first inner shell monomer; and a second inner shell, wherein the second inner shell comprises, as polymerized units, 90 to 99.5 wt %, based on weight of the second inner shell, of a non-ionic ethylenically unsaturated second inner shell monomer; and 0.5 to 10 wt %, based on weight of the second inner shell, of an aliphatic second inner shell monomer selected from the group consisting of allyl acrylate, allyl methacrylate and mixtures thereof; and (iii) an outer shell, wherein the outer shell comprises, as polymerized units, 10 to 45 wt %, based on weight of the outer shell, of a non-ionic ethylenically unsaturated outer shell monomer; 50 to 88.9 wt %, based on weight of the outer shell, of an aliphatic outer shell monomer selected from the group consisting of allyl acrylate, allyl methacrylate and mixtures thereof; 0.1 to 10 wt %, based on weight of the outer shell, of a monoethylenically unsaturated non-carboxylic acid outer shell monomer; and, 1 to 25 wt %, based on weight of the outer shell, of an ethylenically unsaturated surfactant outer shell monomer; wherein the core, when dry, contains at least one void; wherein the multistage polymeric particle has an average particle size, when dry, of 50 to 1,000 nm; and wherein the multistage polymeric particle contains less than 0.001 wt %, based on weight of the multistage polymeric particle, of polymerized units of styrene monomer in the backbone chain of the core, the inner shell and the outer shell combined.

The present invention provides a suncare formulation, comprising: a dermatologically acceptable organic carrier; a UV radiation absorbing agent; an SPF booster, wherein the SPF booster comprises a multistage polymeric particle, comprising: (i) a core, wherein the core comprises, as polymerized units, 20 to 60 wt %, based on weight of the core, of a monoethylenically unsaturated carboxylic acid core monomer; and 40 to 80 wt %, based on weight of the core, of a non-ionic ethylenically unsaturated core monomer; (ii) an inner shell, wherein the inner shell comprises: a first inner shell, wherein the first inner shell comprises, as polymerized units, 90 to 99.9 wt %, based on weight of the first inner shell, of a non-ionic ethylenically unsaturated first inner shell monomer; and 0.1 to 10 wt %, based on weight of the first inner shell, a monoethylenically unsaturated carboxylic acid first inner shell monomer; and a second inner shell, wherein the second inner shell comprises, as polymerized units, 90 to 99.5 wt %, based on weight of the second inner shell, of a non-ionic ethylenically unsaturated second inner shell monomer; and 0.5 to 10 wt %, based on weight of the second inner shell, of an aliphatic second inner shell monomer selected from the group consisting of allyl acrylate, allyl methacrylate and mixtures thereof; and (iii) an outer shell, wherein the outer shell comprises, as polymerized units, 10 to 45 wt %, based on weight of the outer shell, of a non-ionic ethylenically unsaturated outer shell monomer; 50 to 88.9 wt %, based on weight of the outer shell, of an aliphatic outer shell monomer selected from the group consisting of allyl acrylate, allyl methacrylate and mixtures thereof; 0.1 to 10 wt %, based on weight of the outer shell, of a monoethylenically unsaturated non-carboxylic acid outer shell monomer; and, 1 to 25 wt %, based on weight of the outer shell, of an ethylenically unsaturated surfactant outer shell monomer, wherein the ethylenically unsaturated surfactant outer shell monomer is selected from the group consisting of an anionic surfactant monomer according to Formula I, a non-ionic surfactant monomer according to Formula II and mixtures thereof;

particle, of polymerized units of styrene monomer in the backbone chain of the core, the inner shell and the outer shell combined.

DETAILED DESCRIPTION

We have surprisingly found that the alcohol based suncare formulations of the present invention containing UV absorbing agents and an SPF booster, wherein the SPF booster, multistage polymeric particle provide SPF boosting when incorporated into the alcohol based sunscreen formulation, wherein the multistage polymer particles, comprise: (i) a core, wherein the core comprises, as polymerized units, a monoethylenically unsaturated carboxylic acid core monomer and a non-ionic ethylenically unsaturated core monomer; (ii) an inner shell, wherein the inner shell comprises, as polymerized units, a non-ionic ethylenically unsaturated inner shell monomer; a monoethylenically unsaturated carboxylic acid inner shell monomer and an aliphatic inner shell monomer; (iii) an outer shell, wherein the outer shell comprises, as polymerized units, a non-ionic ethylenically

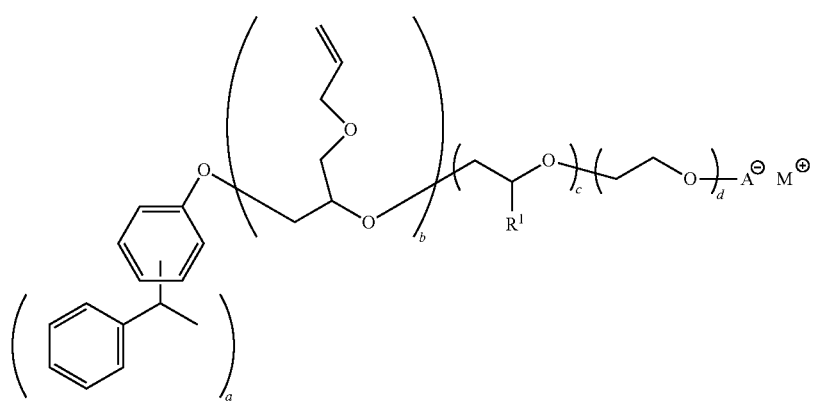

(I)

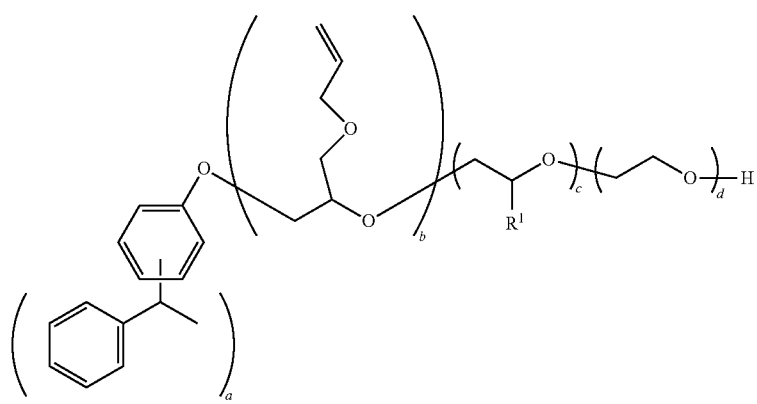

(II)

wherein a is an average of 1-3; wherein b is an average of 1-3; wherein c is an average of 0-5; wherein d is 4-100; wherein A is an anion; wherein M is a cation charge balancing the anion; wherein the core, when dry, contains at least one void; wherein the multistage polymeric particle has an average particle size, when dry, of 50 to 1,000 nm; and wherein the multistage polymeric particle contains less than 0.001 wt %, based on weight of the multistage polymeric unsaturated outer shell monomer; an aliphatic outer shell monomer; a monoethylenically unsaturated non-carboxylic acid outer shell monomer and an ethylenically unsaturated surfactant outer shell monomer; wherein the core, when dry, contains at least one void; and wherein the multistage polymeric particle has an average particle size, when dry, of 50 to 1,000 nm; and facilitating more desirable aesthetics to the suncare formulation.

Unless otherwise indicated, ratios, percentages, parts, and the like are by weight.

The term "polymerized units" as used herein and in the appended claims refers to the remnant of the indicated monomer; thus a structural unit of ethyl acrylate is illustrated:

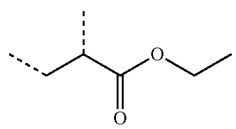

where the dotted lines represent the points of attachment to the polymer backbone.

The term "(meth)acrylic acid" as used herein and in the appended claims is intended to serve as a generic expression embracing both acrylic acid and methacrylic acid.

The term "(meth)acrylate" as used herein and in the appended claims is intended to serve as a generic expression embracing both acrylate and methacrylate.

The term "(meth)acrylamide" as used herein and in the appended claims is intended to serve as a generic expression embracing both acrylamide and methacrylamide.

The term "(meth)acryloxypropionic acid" as used herein and in the appended claims is intended to serve as a generic expression embracing both acryloxypropionic acid and methacryloxypropionic acid.

The term "dermatologically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the suncare formulation of the present invention, comprises a dermatologically acceptable organic carrier; a UV radiation absorbing agent; an SPF booster, wherein the SPF booster comprises a multistage polymeric particle, comprising: (i) a core, wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer; (ii) an inner shell, wherein the inner shell comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0.05 to 9.99 wt % (preferably, 0.5 to 8 wt %; more preferably, 1 to 6 wt %; most preferably, 1.5 to 5 wt %), based on weight of the inner shell, of an aliphatic inner shell monomer selected from the group consisting of allyl acrylate, allyl methacrylate and mixtures thereof; (iii) an outer shell, wherein the outer shell comprises, as polymerized units, 10 to 45 wt % (preferably, 15 to 40 wt %; more preferably, 17.5 to 37.5 wt %; most preferably, 20 to 35 wt %), based on weight of the outer shell, of a non-ionic ethylenically unsaturated outer shell monomer; 50 to 88.9 wt % (preferably, 50 to 80 wt %; more preferably, 50 to 75 wt %; most preferably, 55 to 65 wt %), based on weight of the outer shell, of an aliphatic outer shell monomer selected from the group consisting of allyl acrylate, allyl methacrylate and mixtures thereof; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; and, 1 to 25 wt % (preferably, 2 to 20 wt %; more preferably, 2.5 to 17.5 wt %; most preferably, 3 to 15 wt %), based on weight of the outer shell, of an ethylenically unsaturated surfactant outer shell monomer; wherein the core, when dry, contains at least one void; and wherein the multistage polymeric particle has an average particle size, when dry, of 50 to 1,000 nm.

Preferably, the suncare formulation of the present invention, comprises a dermatologically acceptable organic carrier. More preferably, the suncare formulation of the present invention, comprises 30 to 92 wt % (preferably, 35 to 92 wt %; more preferably, 40 to 80 wt %) of a dermatologically acceptable organic carrier. Most preferably, the suncare formulation of the present invention, comprises 30 to 92 wt % (preferably, 35 to 92 wt %; more preferably, 40 to 80 wt %) of a dermatologically acceptable organic carrier; wherein the dermatologically acceptable organic carrier is selected to be capable of evaporating upon application of the suncare formulation to the skin. Preferred dermatologically acceptable organic carriers include organic solvents, propellants and combinations thereof.

Preferred organic solvents for use in the suncare formulation of the present invention, include glycol (e.g., ethylene glycol, propylene glycol, butylene glycol, pentylene glycol, hexylene glycol, dipropylene glycol, ethoxydiglycol), $C_{1-4}$ straight or branched chain alcohol (e.g., methyl alcohol, ethyl alcohol, propyl alcohol, isopropyl alcohol, butyl alcohol), acetone, methyl acetate, butyl cellusolve and mixtures thereof.

Preferred propellants for use in the suncare formulation of the present invention, include methane, ethane, propane, isobutane, n-butane, hexane, heptane, dimethyl ether, diethyl ether, fluoro containing materials (e.g., 1,1-difluoroethane, ethyl perfluoroisobutyl ether, ethyl perfluorobutyl ether, methyl perfluoroisobutyl ether, methyl perfluorobutyl ether) and mixtures thereof. Preferred fluoro containing propellants include Cosmetic Fluid CF-76 (INCI designation: ethyl perfluorobutyl ether/ethyl perfluoroisobutyl ether) and Cosmetic Fluid CF-61 (INCI designation: methyl perfluorobutyl ether/methyl perfluoroisobutyl ether).

Preferably, the dermatologically acceptable organic carrier used in the suncare formulation of the present invention, includes an alcohol, wherein the alcohol includes at least one of methyl alcohol, ethyl alcohol and isopropyl alcohol. More preferably, the dermatologically acceptable organic carrier used in the suncare formulation of the present invention, includes an alcohol, wherein the alcohol is a specifically denatured alcohol. Most preferably, the dermatologically acceptable organic carrier includes a specifically denatured ethyl alcohol (e.g., INCI: SD alcohol 40-B).

Preferably, the suncare formulation of the present invention, comprises a UV radiation absorbing agent. More preferably, the suncare formulation of the present invention, comprises 0.1 to 70 wt % (preferably, 5 to 65 wt %; more preferably, 7.5 to 60 wt %; most preferably, 10 to 55 wt %) of a UV radiation absorbing agent. Still more preferably, the suncare formulation of the present invention, comprises 0.1 to 70 wt % (preferably, 5 to 65 wt %; more preferably, 7.5 to 60 wt %; most preferably, 10 to 55 wt %) of a UV radiation absorbing agent; wherein the UV radiation absorbing agent is selected from the group including physical blockers (e.g., red petrolatum, titanium dioxide, zinc oxide) and chemical absorbers (e.g., 1-(4-methoxyphenol)-3-(4-tert-butylphenyl)propane-1,3-dione (INCI: avobenzone), 2-hydroxy-4-methoxybenzophenone (INCI: oxybenzone); dioxybenzone; sulisobenzone; menthyl anthranilate; para-aminobenzoic acid; amyl paradimethylaminobenzoic acid; octyl para-dimethylaminobenzoate; ethyl 4-bis (hydroxypropyl) para-aminobenzoate; polyethylene glycol (PEG-25) para-aminobenzoate; ethyl 4-bis (hydroxypropyl) aminobenzoate; diethanolamine para-methyoxycinnamate; 2-ethoxyethyl para-methoxycinnamate; ethylhexyl para-methoxycinnamate; octyl para-methoxycinnamate; isoamyl para-methoxycinnamate; 2-ethylhexyl-2-cyano-3,3-diphenyl-acrylate; 2-ethylhexyl-2-cyano-3,3-diphenyl-2-propenoate (INCI: octocrylene); 2-ethylhexyl salicylate (INCI: octisalate); homomenthyl salicylate; glyceryl aminobenzoate; triethanolamine salicylate; digalloyl trioleate; lawsone with dihydroxyacetone; 2-phenylbenzimidazole-5-sulfonic acid; 4-methylbenzylidine camphor; avobenzone; triazines; benzotriazoles; vinyl group-containing amides; cinnamic acid amides; sulfonated benzimidazoles); 3,3,5-trimethylcyclohexyl 2-hydroxybenzoate (INCI: Homosalate). Yet more preferably, the suncare formulation of the present invention, comprises 0.1 to 70 wt % (preferably, 5 to 65 wt %; more preferably, 7.5 to 60 wt %; most preferably, 10 to 55 wt %) of a UV radiation absorbing agent, wherein the UV radiation absorbing agent comprises a mixture of UV radiation absorbing agents. Yet still more preferably, the suncare formulation of the present invention, comprises 0.1 to 70 wt % (preferably, 5 to 65 wt %; more preferably, 7.5 to 60 wt %; most preferably, 10 to 55 wt %) of a UV radiation absorbing agent, wherein the UV absorbing agent is a mixture of UV absorbing agents including at least one of 1-(4-methoxyphenol)-3-(4-tert-butylphenyl)propane-1,3-dione (INCI: avobenzone); 2-ethylhexyl 2-hydroxybenzoate (INCI: octisalate); 2-ethyhexyl-2-cyano-3,3-diphenyl-2-propenoate (INCI: octocrylene); 2-hydroxy-4-methoxybenzophenone (INCI: oxybenzone) and 3,3,5-trimethylcyclohexyl 2-hydroxybenzoate (INCI: Homosalate). Most preferably, the suncare formulation of the present invention, comprises 0.1 to 70 wt % (preferably, 5 to 65 wt %; more preferably, 7.5 to 60 wt %; most preferably, 10 to 55 wt %) of a UV radiation absorbing agent, wherein the UV absorbing agent is a mixture of UV absorbing agents including 1-(4-methoxyphenol)-3-(4-tert-butylphenyl)propane-1,3-dione (INCI: avobenzone); 2-ethylhexyl 2-hydroxybenzoate (INCI: octisalate); 2-ethyhexyl-2-cyano-3,3-diphenyl-2-propenoate (INCI: octocrylene); and 2-hydroxy-4-methoxybenzophenone (INCI: oxybenzone).

Preferably, the suncare formulation of the present invention, comprises an SPF booster; wherein the SPF booster comprises a multistage polymeric particle. More preferably, the suncare formulation of the present invention, comprises 0.5 to 20 wt % (preferably, 1 to 15 wt %; more preferably, 1.5 to 10 wt %; most preferably, 2 to 5 wt %) of an SPF booster; wherein the SPF booster comprises a multistage polymeric particle. Most preferably, the suncare formulation of the present invention, comprises 0.5 to 20 wt % (preferably, 1 to 15 wt %; more preferably, 1.5 to 10 wt %; most preferably, 2 to 5 wt %) of an SPF booster; wherein the SPF booster comprises a multistage polymeric particle, comprising: (i) a core, wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer; (ii) an inner shell, wherein the inner shell comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0.05 to 9.99 wt % (preferably, 0.5 to 8 wt %; more preferably, 1 to 6 wt %; most preferably, 1.5 to 5 wt %), based on weight of the inner shell, of an aliphatic inner shell monomer selected from the group consisting of allyl acrylate, allyl methacrylate and mixtures thereof; (iii) an outer shell, wherein the outer shell comprises, as polymerized units, 10 to 45 wt % (preferably, 15 to 40 wt %; more preferably, 17.5 to 37.5 wt %; most preferably, 20 to 35 wt %), based on weight of the outer shell, of a non-ionic ethylenically unsaturated outer shell monomer; 50 to 88.9 wt % (preferably, 50 to 80 wt %; more preferably, 50 to 75 wt %; most preferably, 55 to 65 wt %), based on weight of the outer shell, of an aliphatic outer shell monomer selected from the group consisting of allyl acrylate, allyl methacrylate and mixtures thereof; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; and, 1 to 25 wt % (preferably, 2.5 to 20 wt %; more preferably, 4 to 17.5 wt %; most preferably, 5 to 15 wt %), based on weight of the outer shell, of an ethylenically unsaturated surfactant outer shell monomer; wherein the core, when dry, contains at least one void; wherein the multistage polymeric particle has an average particle size, when dry, of 50 to 1,000 nm (400 to 900 nm; 450 to 850 nm; 500 to 800).

Preferably, the multistage polymeric particle, comprises a core, wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer. More preferably, the multistage polymeric particle, comprises 1 to 25 wt %, based on weight of the multistage polymeric particle, of a core; wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer. Still more preferably, the multistage polymeric particle, comprises 2 to 12 wt %, based on weight of the multistage polymeric particle, of a core; wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer. Yet still more preferably, the multistage polymeric particle, comprises 3 to 10 wt %, based on weight of the multistage polymeric particle, of a core; wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer;

and 40 to 80 wt % (preferably, 50 to 70 wt %; more preferably, 55 to 65 wt %), based on weight of the core, of a non-ionic ethylenically unsaturated core monomer. Most preferably, the multistage polymeric particle, comprises 3.5 to 7.5 wt %, based on weight of the multistage polymeric particle, of a core; wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer.

Preferably, the monoethylenically unsaturated carboxylic acid core monomer is selected from monoethylenically unsaturated monomers that contain at least one carboxylic acid group. More preferably, the monoethylenically unsaturated carboxylic acid core monomer is selected from the group consisting of (meth)acrylic acid, (meth)acryloxypropionic acid, itaconic acid, aconitic acid, maleic acid, maleic anhydride, fumaric acid, crotonic acid, citraconic acid, maleic anhydride, monomethyl maleate, monomethyl fumarate, monomethyl itaconate, and other derivatives such as corresponding anhydride, amides, and esters. Still more preferably, the monoethylenically unsaturated carboxylic acid core monomer is selected from the group consisting of acrylic acid, methacrylic acid and mixtures thereof. Yet still more preferably, the monoethylenically unsaturated carboxylic acid core monomer includes methacrylic acid. Most preferably, the monoethylenically unsaturated carboxylic acid core monomer is methacrylic acid.

Preferably, the non-ionic ethylenically unsaturated core monomer is selected from the group consisting of ethylene, vinyl acetate, vinyl chloride, vinylidene chloride acrylonitrile, (meth)acrylamide, methyl (meth)acrylate, ethyl (meth)acrylate, n-butyl (meth)acrylate, i-butyl (meth)acrylate, t-butyl (meth)acrylate, cyclo-hexyl (meth)acrylate, 2-ethylhexyl (meth)acrylate, lauryl (meth)acrylate, oleyl (meth)acrylate, palmityl (meth)acrylate, stearyl (meth)acrylate and mixtures thereof. More preferably, the non-ionic ethylenically unsaturated core monomer is selected from the group consisting of methyl methacrylate, butyl acrylate and mixtures thereof. Still more preferably, the non-ionic ethylenically unsaturated core monomer includes methyl methacrylate. Most preferably, the non-ionic ethylenically unsaturated core monomer is methyl methacrylate.

Preferably, the multistage polymeric particle, comprises an inner shell, wherein the inner shell comprises 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0.05 to 9.99 wt % (preferably, 0.5 to 8 wt %; more preferably, 1 to 6 wt %; most preferably, 1.5 to 5 wt %), based on weight of the inner shell, of an aliphatic inner shell monomer selected from the group consisting of allyl acrylate, allyl methacrylate and mixtures thereof. More preferably, the multistage polymeric particle, comprises 15 to 80 wt %, based on weight of the multistage polymeric particle, of an inner shell, wherein the inner shell comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt % more preferably, 0.1 to 5 wt %; most preferably, 0.2 to 4 wt %), based on weight of the inner shell, a monoethylenically unsaturated carboxylic acid inner shell monomer; and 0.05 to 9.99 wt % (preferably, 0.5 to 8 wt %; more preferably, 1 to 6 wt %; most preferably, 1.5 to 5 wt %), based on weight of the inner shell, of an aliphatic inner shell monomer selected from the group consisting of allyl acrylate, allyl methacrylate and mixtures thereof. Still more preferably, the multistage polymeric particle, comprises 25 to 75 wt %, based on weight of the multistage polymeric particle, of an inner shell, wherein the inner shell comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0.05 to 9.99 wt % (preferably, 0.5 to 8 wt %; more preferably, 1 to 6 wt %; most preferably, 1.5 to 5 wt %), based on weight of the inner shell, of an aliphatic inner shell monomer selected from the group consisting of allyl acrylate, allyl methacrylate and mixtures thereof. Yet still more preferably, the multistage polymeric particle, comprises 30 to 60 wt %, based on weight of the multistage polymeric particle, of an inner shell, wherein the inner shell comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0.05 to 9.99 wt % (preferably, 0.5 to 8 wt %; more preferably, 1 to 6 wt %; most preferably, 1.5 to 5 wt %), based on weight of the inner shell, of an aliphatic inner shell monomer selected from the group consisting of allyl acrylate, allyl methacrylate and mixtures thereof. Most preferably, the multistage polymeric particle, comprises 40 to 50 wt %, based on weight of the multistage polymeric particle, of an inner shell, wherein the inner shell comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0.05 to 9.99 wt % (preferably, 0.5 to 8 wt %; more preferably, 1 to 6 wt %; most preferably, 1.5 to 5 wt %), based on weight of the inner shell, of an aliphatic inner shell monomer selected from the group consisting of allyl acrylate, allyl methacrylate and mixtures thereof.

Preferably, the non-ionic ethylenically unsaturated inner shell monomer is selected from the group consisting of acrylonitrile, (meth)acrylamide, methyl (meth)acrylate, ethyl (meth)acrylate, n-butyl (meth)acrylate, i-butyl (meth)acrylate, t-butyl (meth)acrylate, cyclo-hexyl (meth)acrylate, 2-ethylhexyl (meth)acrylate, lauryl (meth)acrylate, oleyl (meth)acrylate, palmityl (meth)acrylate, stearyl (meth)acrylate, and iso-bornyl (meth)acrylate. More preferably, the non-ionic ethylenically unsaturated inner shell monomer is selected from the group consisting of methyl acrylate, methyl methacrylate, ethyl acrylate, ethyl methacrylate, butyl acrylate, butyl methacrylate, isobutyl acrylate, isobutyl methacrylate, hydroxyethyl methacrylate, hydroxypropyl methacrylate, dimethylaminoethyl methacrylate, dimethylaminopropyl methacrylamide and mixtures thereof. Still more preferably, the non-ionic ethylenically unsaturated inner shell monomer is selected from the group consisting of at least one of butyl methacrylate and methyl methacrylate. Most preferably, the non-ionic ethylenically unsaturated inner shell monomer includes both butyl methacrylate and methyl methacrylate.

Preferably, the monoethylenically unsaturated carboxylic acid inner shell monomer is selected from monoethylenically unsaturated monomers that contain at least one carboxylic acid group. More preferably, the monoethylenically unsaturated carboxylic acid inner shell monomer is selected from the group consisting of (meth)acrylic acid, (meth) acryloxypropionic acid, itaconic acid, aconitic acid, maleic acid, fumaric acid, crotonic acid, citraconic acid, maleic anhydride monomethyl maleate, monomethyl fumarate, monomethyl itaconate, derivatives thereof (e.g., corresponding anhydride, amides, esters) and mixtures thereof. Still more preferably, the monoethylenically unsaturated carboxylic acid inner shell monomer is selected from the group consisting of acrylic acid, methacrylic acid and mixtures thereof. Yet still more preferably, the monoethylenically unsaturated carboxylic acid inner shell monomer includes methacrylic acid. Most preferably, the monoethylenically unsaturated carboxylic acid inner shell monomer is methacrylic acid.

Preferably, the aliphatic inner shell monomer is selected from the group consisting of allyl acrylate, allyl methacrylate and mixtures thereof. More preferably, the aliphatic inner shell monomer includes allyl methacrylate. Most preferably, the aliphatic inner shell monomer is allyl methacrylate.

Preferably, the multistage polymeric particle, comprises an inner shell, wherein the inner shell includes multiple inner shells. More preferably, the multistage polymeric particle, comprises an inner shell, wherein the inner shell includes: a first inner shell and a second inner shell. Most preferably, the multistage polymeric particle, comprises an inner shell, wherein the inner shell includes: (a) a first inner shell, wherein the first inner shell comprises, as polymerized units, 90 to 99.9 wt % (preferably, 92.5 to 99.5 wt %; more preferably, 95 to 99 wt %; most preferably, 96 to 98 wt %), based on weight of the first inner shell, of a non-ionic ethylenically unsaturated first inner shell monomer (preferably, wherein the non-ionic ethylenically unsaturated first inner shell monomer is selected from the group consisting of butyl methacrylate, methyl methacrylate and mixtures thereof; more preferably, wherein the non-ionic ethylenically unsaturated first inner shell monomer includes both butyl methacrylate and methyl methacrylate; most preferably, wherein the non-ionic ethylenically unsaturated first inner shell monomer is a mixture of butyl methacrylate and methyl methacrylate); and 0.1 to 10 wt % (preferably, 0.5 to 7.5 wt %; more preferably, 1 to 5 wt %; most preferably, 2 to 4 wt %), based on weight of the first inner shell, a monoethylenically unsaturated carboxylic acid first inner shell monomer (preferably, wherein the monoethylenically unsaturated carboxylic acid first inner shell monomer is selected from the group consisting of acrylic acid, methacrylic acid and mixtures thereof; more preferably, wherein the monoethylenically unsaturated carboxylic acid first inner shell monomer includes methacrylic acid; most preferably, wherein the monoethylenically unsaturated carboxylic acid first inner shell monomer is methacrylic acid); and (b) a second inner shell, wherein the second inner shell comprises, as polymerized units, 90 to 99.5 wt % (preferably, 92 to 99 wt %; more preferably, 94 to 98 wt %; most preferably, 95 to 97.5 wt %), based on weight of the second inner shell, of a non-ionic ethylenically unsaturated second inner shell monomer (preferably, wherein the non-ionic ethylenically unsaturated second inner shell monomer includes methyl methacrylate; more preferably, wherein the non-ionic ethylenically unsaturated second inner shell monomer is methyl methacrylate); and 0.5 to 10 wt % (preferably, 1 to 8 wt %; more preferably, 2 to 6 wt %; most preferably, 2.5 to 5 wt %), based on weight of the second inner shell, of an aliphatic second inner shell monomer selected from the group consisting of allyl acrylate, allyl methacrylate and mixtures thereof (preferably, wherein the aliphatic second inner shell monomer is allyl methacrylate).

Preferably, the multistage polymeric particle, comprises an outer shell, wherein the outer shell comprises, as polymerized units, 10 to 45 wt % (preferably, 15 to 40 wt %; more preferably, 17.5 to 37.5 wt %; most preferably, 20 to 35 wt %), based on weight of the outer shell, of a non-ionic ethylenically unsaturated outer shell monomer; 50 to 88.9 wt % (preferably, 50 to 80 wt %; more preferably, 50 to 75 wt %; most preferably, 55 to 65 wt %), based on weight of the outer shell, of an aliphatic outer shell monomer selected from the group consisting of allyl acrylate, allyl methacrylate and mixtures thereof; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; and, 1 to 25 wt % (preferably, 2 to 20 wt %; more preferably, 2.5 to 17.5 wt %; most preferably, 3 to 15 wt %), based on weight of the outer shell, of an ethylenically unsaturated surfactant outer shell monomer. More preferably, the multistage polymeric particle, comprises 15 to 80 wt %, based on weight of the multistage polymeric particle, of an outer shell, wherein the outer shell comprises, as polymerized units, 10 to 45 wt % (preferably, 15 to 40 wt %; more preferably, 17.5 to 37.5 wt %; most preferably, 20 to 35 wt %), based on weight of the outer shell, of a non-ionic ethylenically unsaturated outer shell monomer; 50 to 88.9 wt % (preferably, 50 to 80 wt %; more preferably, 50 to 75 wt %; most preferably, 55 to 65 wt %), based on weight of the outer shell, of an aliphatic outer shell monomer selected from the group consisting of allyl acrylate, allyl methacrylate and mixtures thereof; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; and, 1 to 25 wt % (preferably, 2 to 20 wt %; more preferably, 2.5 to 17.5 wt %; most preferably, 3 to 15 wt %), based on weight of the outer shell, of an ethylenically unsaturated surfactant outer shell monomer. Still more preferably, the multistage polymeric particle, comprises 25 to 75 wt %, based on weight of the multistage polymeric particle, of an outer shell, wherein the outer shell comprises, as polymerized units, 10 to 45 wt % (preferably, 15 to 40 wt %; more preferably, 17.5 to 37.5 wt %; most preferably, 20 to 35 wt %), based on weight of the outer shell, of a non-ionic ethylenically unsaturated outer shell monomer; 50 to 88.9 wt % (preferably, 50 to 80 wt %; more preferably, 50 to 75 wt %; most preferably, 55 to 65 wt %), based on weight of the outer shell, of an aliphatic outer shell monomer selected from the group consisting of allyl acrylate, allyl methacrylate and mixtures thereof; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; and, 1 to 25 wt % (preferably, 2 to 20 wt %; more preferably, 2.5 to 17.5 wt %; most preferably, 3 to 15 wt %), based on weight of the outer shell, of an ethylenically unsaturated surfactant outer shell monomer. Yet still more preferably, the multistage polymeric particle, comprises 30 to 60 wt %, based on weight of the multistage polymeric particle, of an outer shell, wherein the outer shell comprises, as polymerized units, 10 to 45 wt % (preferably, 15 to 40 wt %; more preferably, 17.5 to 37.5 wt %; most preferably, 20 to 35 wt %), based on weight of the outer shell, of a non-ionic ethylenically unsaturated outer shell monomer; 50 to 88.9 wt % (preferably, 50 to 80 wt %; more preferably, 50 to 75 wt %; most preferably, 55 to 65 wt %), based on weight of the outer shell, of an aliphatic outer shell monomer selected from the group consisting of allyl acrylate, allyl methacrylate and mixtures thereof; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; and, 1 to 25 wt % (preferably, 2 to 20 wt %; more preferably, 2.5 to 17.5 wt %; most preferably, 3 to 15 wt %), based on weight of the outer shell, of an ethylenically unsaturated surfactant outer shell monomer. Most preferably, the multistage polymeric particle, comprises 40 to 50 wt %, based on weight of the multistage polymeric particle, of an outer shell, wherein the outer shell comprises, as polymerized units, 10 to 45 wt % (preferably, 15 to 40 wt %; more preferably, 17.5 to 37.5 wt %; most preferably, 20 to 35 wt %), based on weight of the outer shell, of a non-ionic ethylenically unsaturated outer shell monomer; 50 to 88.9 wt % (preferably, 50 to 80 wt %; more preferably, 50 to 75 wt %; most preferably, 55 to 65 wt %), based on weight of the outer shell, of an aliphatic outer shell monomer selected from the group consisting of allyl acrylate, allyl methacrylate and mixtures thereof; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; and, 1 to 25 wt % (preferably, 2 to 20 wt %; more preferably, 2.5 to 17.5 wt %; most preferably, 3 to 15 wt %), based on weight of the outer shell, of an ethylenically unsaturated surfactant outer shell monomer.

Preferably, the non-ionic ethylenically unsaturated outer shell monomer is selected from the group consisting of acrylonitrile, (meth)acrylamide, methyl (meth)acrylate, ethyl (meth)acrylate, n-butyl (meth)acrylate, i-butyl (meth)acrylate, t-butyl (meth)acrylate, cyclo-hexyl (meth)acrylate, 2-ethylhexyl (meth)acrylate, lauryl (meth)acrylate, oleyl (meth)acrylate, palmityl (meth)acrylate, stearyl (meth)acrylate, and iso-bornyl (meth)acrylate. More preferably, the non-ionic ethylenically unsaturated outer shell monomer is selected from the group consisting of methyl acrylate, methyl methacrylate, ethyl acrylate, ethyl methacrylate, butyl acrylate, butyl methacrylate, isobutyl acrylate, isobutyl methacrylate, hydroxyethyl methacrylate, hydroxypropyl methacrylate, dimethylaminoethyl methacrylate, dimethylaminopropyl methacrylamide and mixtures thereof. Still more preferably, the a non-ionic ethylenically unsaturated outer shell monomer includes methyl methacrylate. Most preferably, the non-ionic ethylenically unsaturated outer shell monomer is methyl methacrylate.

Preferably, the aliphatic outer shell monomer is selected from the group consisting of allyl acrylate, allyl methacrylate and mixtures thereof. More preferably, the aliphatic outer shell monomer includes allyl methacrylate. Most preferably, the aliphatic outer shell monomer is allyl methacrylate.

Preferably, the monoethylenically unsaturated non-carboxylic acid outer shell monomer is selected from monoethylenically unsaturated monomers containing at least one non-carboxylic acid type acid group. More preferably, the monoethylenically unsaturated non-carboxylic acid outer shell monomer is selected from the group consisting of allyl sulfonic acid, allyl phosphonic acid, allyl oxybenzene sulfonic acid, 2-acrylamido-2-methylpropane sulfonic acid, 2-hydroxy-3-2-propenyloxy)propane sulfonic acid, 2-methyl-2-propene-1-sulfonic acid, 2-methacrylamido-2-methyl-1-propane sulfonic acid, 3-methacrylamido-2-hydroxy-1-propane sulfonic acid, 3-sulfopropyl acrylate, 3-sulfopropyl methacrylate, isopropenyl phosphonic acid, vinyl phosphonic acid, phosphoethyl methacrylate, styrene sulfonic acid, vinyl sulfonic acid, alkali metal salts thereof, ammonium salts thereof and mixtures thereof. Still more preferably, the monoethylenically unsaturated non-carboxylic acid outer shell monomer is selected from the group consisting of 2-acrylamido-2-methylpropane sulfonic acid, styrene sulfonic acid, sodium styrene sulfonate and mixtures thereof. Yet still more preferably, the monoethylenically unsaturated non-carboxylic acid outer shell monomer includes sodium styrene sulfonate. Most preferably, the monoethylenically unsaturated non-carboxylic acid outer shell monomer is sodium styrene sulfonate.

Preferably, the ethylenically unsaturated surfactant outer shell monomer is selected from the group consisting of an anionic surfactant monomer, a non-ionic surfactant monomer and mixtures thereof. More preferably, the ethylenically unsaturated surfactant outer shell monomer includes an anionic surfactant monomer. Most preferably, the ethylenically unsaturated surfactant outer shell monomer is an anionic surfactant monomer.

Preferably, the anionic surfactant monomer is selected from the group of anionic surfactant monomers of Formula I

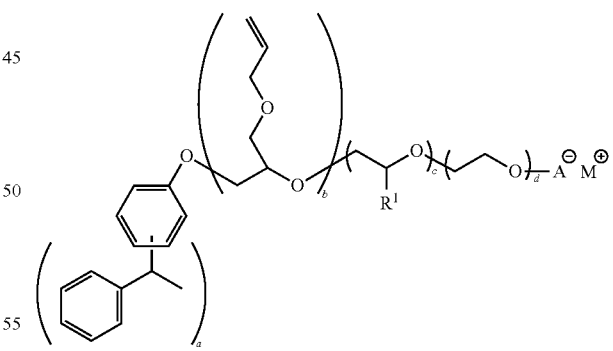

wherein a is an average of 1-3 (preferably, 1-2; most preferably 2); wherein b is an average of 1-3 (preferably, 2-3; most preferably, 2); wherein c is an average of 0-5 (preferably, 0-2; most preferably, 0); wherein d is 4-100 (preferably, 5-50; more preferably, 7.5 to 20; most preferably, 10 to 20); wherein A is an anion (preferably, a $SO_3^-$ or a $PO_3^{2-}$; more preferably, $SO_3^-$); and wherein M is a cation (preferably, a $Na^+$, $K^+$ or an $NH_4^+$; more preferably, $NH_4+$) charge balancing the anion. More preferably, the anionic surfactant monomer is selected from the group of anionic surfactant monomers of Formula I, wherein a is an average of 2, wherein b is an average of 2, wherein c is 0, and wherein d is an average of 10 to 20. Still more preferably, the anionic surfactant monomer is selected from the group of anionic surfactant monomers of Formula I, the anionic surfactant monomer is selected from the group of anionic surfactant monomers of Formula I, wherein a is an average of 2, wherein b is an average of 2, wherein c is 0, wherein d is an average of 10 to 20 and wherein A is $SO_3^-$. Most preferably, the anionic surfactant monomer is selected from the group of anionic surfactant monomers of Formula I, the anionic surfactant monomer is selected from the group of anionic surfactant monomers of Formula I, wherein a is an average of 2, wherein b is an average of 2, wherein c is 0, wherein d is an average of 10 to 20, wherein A is $SO_3^-$ and wherein M is $NH_4^+$.

Preferably, the non-ionic surfactant monomer is selected from the group of non-ionic surfactant monomers of Formula II

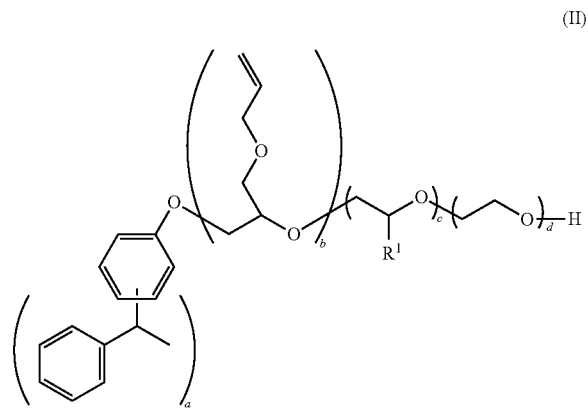

(II)

wherein a is an average of 1-3 (preferably, 1-2; most preferably, 2); wherein b is an average of 1-3 (preferably, 2-3; most preferably, 2); wherein c is an average of 0-5 (preferably, 0-2; most preferably, 0); and wherein d is 4-100 (preferably, 5-50; more preferably, 7.5 to 20; most preferably, 10 to 20).

Preferably, the multistage polymeric particle, comprises an inner shell and an outer shell, wherein the outer shell comprises at least 25 wt % of the combined weight of the inner shell and the outer shell. More preferably, the multistage polymeric particle, comprises an inner shell and an outer shell, wherein the outer shell comprises at least 35 wt % of the combined weight of the inner shell and the outer shell. Most preferably, the multistage polymeric particle, comprises an inner shell and an outer shell, wherein the outer shell comprises at least 45 wt % of the combined weight of the inner shell and the outer shell.

Preferably, the multistage polymeric particle, comprises a core, wherein the core, when dry, contains at least one void. More preferably, the multistage polymeric particle, comprises a core, wherein the core, when dry, contains at least one void having a void fraction of 5 to 70 vol %, based on the volume occupied by the multistage polymeric particle. Still more preferably, the multistage polymeric particle, comprises a core, wherein the core, when dry, contains at least one void having a void fraction of 10 to 60 vol %, based on the volume occupied by the multistage polymeric particle. Yet still more preferably, the multistage polymeric particle, comprises a core, wherein the core, when dry, contains at least one void having a void fraction of 20 to 50 vol %, based on the volume occupied by the multistage polymeric particle. Most preferably, the multistage polymeric particle, comprises a core, wherein the core, when dry, contains at least one void having a void fraction of 25 to 45 vol %, based on the volume occupied by the multistage polymeric particle. The void fraction is determined by comparing the volume occupied by a plurality of the multistage polymer particles after compaction from a dilute dispersion in a centrifuge to the volume of non-voided multistage polymeric particles having the same composition.

Preferably, the multistage polymeric particle, comprises an inner shell and an outer shell, wherein the $T_g$ (as measured by DSC) of the inner shell and the outer shell are high enough to support the at least one void contained in the core. More preferably, the multistage polymeric particle, comprises an inner shell and an outer shell, wherein the $T_g$ (as measured by DSC) of at least one of the inner shell and the outer shell is greater than 50° C. Still more preferably, the multistage polymeric particle, comprises an inner shell and an outer shell, wherein the $T_g$ (as measured by DSC) of at least one of the inner shell and the outer shell is greater than 60° C. Most preferably, the multistage polymeric particle, comprises an inner shell and an outer shell, wherein the $T_g$ (as measured by DSC) of at least one of the inner shell and the outer shell is greater than 70° C.

Preferably, the multistage polymeric particles have an average particle size, when dry, of 50 to 1,000 nm, as measured by a Brookhaven BI-90. More preferably, the multistage polymeric particles have an average particle size, when dry, of 400 to 900 nm, as measured by a Brookhaven BI-90. Still more preferably, the multistage polymeric particles have an average particle size, when dry, of 450 to 850 nm, as measured by a Brookhaven BI-90. Most preferably, the multistage polymeric particles have an average particle size, when dry, of 500 to 800 nm, as measured by a Brookhaven BI-90.

Preferably, the multistage polymeric particle contains, as polymerized units, less than 5 wt %, based on weight of the multistage polymeric particle, of total styrene monomer in the backbone chain of the core, the inner shell and the outer shell combined styrene. More preferable, the multistage polymeric particle contains, as polymerized units, less than 2.5 wt %, based on weight of the multistage polymeric particle, of total styrene monomer in the backbone chain of the core, the inner shell and the outer shell combined styrene. Yet more preferably, the multistage polymeric particle is substantially free (i.e., less than 0.001 wt % (preferably, less than 0.0001 wt %; most preferably, less than 1 part per million by weight) based on weight of the multistage polymeric particle) of polymerized units of styrene monomer in the backbone chain of the core, the inner shell and the outer shell combined. Most preferably, the multistage polymeric particle is free (i.e., contains 0 wt %, based on weight of the multistage polymeric particle) of polymerized units of styrene monomer in the backbone chain of the core, the inner shell and the outer shell combined.

Preferably, the multistage polymeric particles are prepared using conventional polymerization techniques. More preferably, the multistage polymeric particles are prepared using a single polymerization step or a sequence of polymerization steps. Still more preferably, the multistage polymeric particles are prepared via a sequential emulsion polymerization process. Preferably, the monomers used in the emulsion polymerization of the shell(s) comprise one or more non-ionic ethylenically unsaturated monomer(s).

Aqueous emulsion polymerization processes are typically conducted in an aqueous reaction mixture, which contains at least one monomer and various synthesis adjuvants, such as free radical sources, buffers, chain transfer agents and reductants in an aqueous reaction medium. The aqueous reaction medium is the continuous fluid phase of the aqueous reaction mixture and contains more than 50 weight % water and optionally one or more water miscible solvents, based on the weight of the aqueous reaction medium. Suitable water miscible solvents include, for example, methanol, ethanol, propanol, acetone, ethylene glycol ethyl ethers, propylene glycol propyl ethers, and diacetone alcohol.

Preferably, in the process of manufacturing the multistage polymeric particles, the void is formed by swelling the core with a swelling agent containing one or more volatile components. The swelling agent permeates the shell(s) to swell the core. The volatile components of the swelling agent can then be removed by drying the multistage polymeric particles, causing a void to be formed within the core. Preferably, the swelling agent includes an aqueous base, such as, for example ammonia, ammonium hydroxide, alkali metal hydroxides (e.g., sodium hydroxide) and volatile amines (e.g., trimethylamine, triethylamine).

Preferably, the multistage polymeric particles are dried before incorporation into the suncare formulation of the present invention. More preferably, the multistage polymeric particles of the present invention are spray dried before incorporation into the suncare formulation of the present invention using well known processing techniques.

Preferably, the suncare formulation of the present invention has an SPF of >10. More preferably, the suncare formulation of the present invention has an SPF of >15. Still more preferably, the suncare formulation of the present invention has an SPF of >20. Most preferably, the suncare formulation of the present invention has an SPF of >30.

Preferably, the suncare formulation of the present invention contains less than 5 wt % water. More preferably, the suncare formulation of the present invention contains less than 4 wt % water. Most preferable, the suncare composition of the present invention contains less than 3 wt % water.

Preferably, the suncare formulation of the present invention is formulated for application to skin using a mechanical device (e g, manual pump spray containers, squeeze bottles) or a pressurized aerosol container (e.g., bag-on-valve container, pressurized can) to generate a spray.

Preferably, the suncare formulation of the present invention, further comprises an optional additive. More preferably, the suncare formulation of the present invention, further comprises an optional additive, wherein the optional additive is selected from the group consisting of film forming agent, water proofing agents, emollients, preservatives, antioxidants, fragrances, humectants, rheology modifiers, aesthetic modifiers, Vitamins, skin protectants, oils, emulsifiers, surfactants, pearlizers, consistency factors, thickeners, super fatting agents, stabilizers, polymers, silicone compounds, fats, waxes, lectins, phospholipids and mixtures thereof. Most preferably, the suncare formulation of the present invention, further comprises an optional additive, wherein the optional additive includes a film forming agent.

Preferably, the suncare formulation of the present invention, further comprises a film forming agent. More preferably, the suncare formulation of the present invention, further comprises 0.1 to 10 wt % (preferably, 0.5 to 9 wt %; more preferably, 0.7 to 5 wt %) of a film forming agent. Most preferably, the suncare formulation of the present invention, further comprises 0.1 to 10 wt % (preferably, 0.5 to 9 wt %; more preferably, 0.7 to 5 wt %) of a film forming agent; wherein the film forming agent is selected to provide a film barrier upon application of the suncare formulation of the present invention to skin. The purpose of the film barrier is to help maintain the UV radiation absorbing agents on the skin following immersion in water.

Preferred film forming agents include petrolatum, emollient esters, lanolin derivatives (e.g., acetylated lanolins), superfatted oils, cyclomethicone, cyclopentasiloxane, dimethicone, dimethicone derivatives, polyesters, natural and synthetic oils, fatty acids, fatty alcohols, waxes, acrylic copolymers and mixtures thereof. Preferably, the suncare formulation of the present invention, further comprises a film forming agent, wherein the film forming agent includes a mixture of a styrene/acrylate copolymer and a dimethicone.

Dimethicone derivatives include polyoxyethylene derivatized dimethicone, polyoxypropylene derivatized dimethicone, polyoxyethylene/polyoxypropylene derivatized dimethicone and mixtures thereof. The term "polyoxyethylene derivatized dimethicone" as used herein and in the appended claims refers to dimethicone polymers comprising a substituted or unsubstituted polyethylene glycol (PEG) functional group and methicone polymers comprising a substituted or unsubstituted PEG functional group. The substituted or unsubstituted PEG functionalities in the polyoxyethylene derivatized dimethicone can be incorporated either in the polymer backbone, as pendant functionalities or a combination of both.

Acrylic copolymers include acrylamide/acrylic copolymers (e.g., Dermacryl® 79 (INCI: Acrylates/Octyacrylamide copolymer) available from National Starch and Chemical); styrene/acrylate copolymers (e.g., Epitax™ AC powder water resistant polymer (INCI: styrene/acrylate copolymer) available from The Dow Chemical Company).

Certain emollients also exhibit film forming functionality by providing a water-resistant barrier on skin. Emollients with film forming behavior include butyloctyl salicylate (e.g., HallBrite® BHB available form HallStar); fatty acids (e.g., oleic, stearic); fatty alcohols (e.g., cetyl, hexadecyl); esters (e.g., 2,2-dimethyl-1,3-propanediyl diheptanoate (INCI: neopentyl glycol diheptanoate)); alkanes (e.g., mineral oil); ethers (e.g., polyoxypropylene butyl ethers, polyoxypropylene cetyl ethers); natural oils and synthetic oils.

The suncare formulation of the present invention are useful for the protection of skin. Preferably, the suncare formulations of the present invention are useful for the protecting skin from UV damage from exposure to the sun. The suncare formulations of the present invention also preferably provide moisturization to the skin, prevention and treatment of dry skin, protection of sensitive skin, improvement of skin tone and texture, masking imperfections, and inhibition of trans-epidermal water loss. Thus, in one aspect the present invention provides that the suncare formulation can be used in a method for protecting skin from UV damage comprising topically administering the suncare formulation to the skin.

Some embodiments of the present invention will now be described in detail in the following Examples.

Comparative Example C1 and Examples 1-5

Multicomponent Polymeric Particle Compositions

The multicomponent polymeric particles in each of Comparative Example C1 and Examples 1-5, comprised 4.7 wt % of a core, 22.1 wt % of a first inner shell, 26.8 wt % of a second inner shell and 46.4 wt % of an outer shell. The multicomponent polymeric particles in each of Comparative Example C1 and Examples 1-5 all comprised the same composition for the core, the first inner shell and the second inner shell, as described in TABLE 1. The composition of the outer shell of the multicomponent polymeric particles in each of Comparative Example C1 and Examples 1-5 was as described in TABLE 2.

TABLE 1

| Component | Polymerized units of (wt %) | | | |
|---|---|---|---|---|
| Composition | MMA | MAA | BMA | ALMA |
| core | 60.0 | 40.0 | — | — |
| 1$^{st}$ inner shell | 88.5 | 3.0 | 8.5 | — |
| 2$^{nd}$ inner shell | 96.9 | — | — | 3.1 |

MMA = methyl methacrylate
MAA = methacrylic acid
BMA = butyl methacrylate
ALMA = allyl methacrylate

TABLE 2

| Outer Shell Composition | Polymerized units of (wt %) | | | | | | | |
|---|---|---|---|---|---|---|---|---|
| | MMA | ALMA | Styrene | DVB | SSS | Serf 1 | Serf 2 | Serf 3 |
| Comparative Example C1 | 37.3 | 60.0 | — | — | 2.7 | — | — | — |
| Example 1 | 27.3 | 60.0 | — | — | 2.7 | 10.0 | — | — |
| Example 2 | 27.3 | 60.0 | — | — | 2.7 | — | 10.0 | — |
| Example 3 | 27.3 | 60.0 | — | — | 2.7 | — | — | 10.0 |
| Example 4 | 32.3 | 60.0 | — | — | 2.7 | — | — | 5.0 |
| Example 5 | 22.3 | 60.0 | — | — | 2.7 | — | — | 15.0 |

MMA = methyl methacrylate
ALMA = allyl methacrylate
DVB = divinyl benzene
SSS = sodium styrene sulfonate
Serf 1 = surfactant monomer according to Formula I (phosphate ammonium salt) available from Ethox Chemicals as E-Sperse ® RS-1684 reactive surfactant
Serf 2 = surfactant monomer according to Formula II available from Ethox Chemicals as E-Sperse ® RS-1617 reactive surfactant
Serf 3 = surfactant monomer according to Formula I (sulfate ammonium salt) available from Ethox Chemicals as E-Sperse ® RS-1618 reactive surfactant Preparation of Example 1

The multicomponent polymeric particles of Example 1 were prepared by adding 718.1 g of deionized water to a 3 liter, 4 neck round bottom flask equipped with an overhead stirrer, a thermocouple, a heating mantle, an adapter inlet, a Claisen head fitted with a water condenser and a nitrogen inlet. The flask contents were then heated to 84° C. under nitrogen. Then a solution of deionized water (19.1 g), citric acid (0.26 g) and sodium persulfate (1.39 g) was added to the flask. Then an aqueous dispersion (58.6 g) of 31 wt % solids poly (60 MMA/40 MAA) acrylic seed (core) polymer, having an average particle diameter of ~185 to 205 nm, was added to the flask. While maintaining the temperature of the flask contents at 82° C., a monomer emulsion containing deionized water (37.3 g), a 23% aqueous solution of sodium dodecylbenzenesulfonate (SDBS)(1.88 g), MMA (76.7 g), BMA (7.4 g) and MAA (2.6 g) was metered into the flask contents over a period of 90 minutes followed by a deionized water rinse of the transfer lines. Next a solution of sodium persulfate (0.5 g) in deionized water (44.5 g) was added to the flask contents over a period of 90 minutes. The temperature set point for the flask contents was then raised to 90° C., concurrent with the transfer to the flask contents of a second monomer emulsion containing deionized water (58.7 g), a 23% aqueous solution of SDBS (2.10 g), MMA (98.3 g), ALMA (3.2 g) and linseed oil fatty acid (0.60 g) over a period of 30 minutes, minutes followed by a deionized water rinse of the transfer lines. Then, a solution of deionized water (38 g) and 28% aqueous ammonium hydroxide (8.1 g) was added to the flask contents. The flask contents were held for 10 minutes, before adding a third monomer emulsion containing deionized water (54.8 g), a 23% aqueous solution of SDBS (3.91 g), a 29% aqueous solution of E-Sperse® RS-1684 reactive surfactant (61.81 g), ALMA (110.5 g), MMA (50.2 g), sodium styrene sulfonate (5.0 g) to the flask contents at 91° C. over a period of 60 minutes; followed by a deionized water rinse of the transfer lines. Then (3.0 g) of an aqueous solution containing FeSO$_4$.7H$_2$O (0.06 g) and versene (0.6 g) was added to the contents of the flask. Then a solution of t-butylhydrogen peroxide (70%)(2.8 g) in deionized water (8.0 g) was added to the flask contents as a shot. Then a solution of isoascorbic acid (1.4 g) in deionized water (25.2 g) was added to the flask contents over a period of 40 minutes. Then for 30 minutes the flask contents were maintained with a temperature set point at 90° C. before removing the heating source and allowing the flask contents to cool to room temperature providing a latex containing the multicomponent polymer particles.

Preparation of Comparative Example C1 and Examples 2-5

The multicomponent polymeric particles of Comparative Example C1 and Examples 2-5 were prepared using the same process as described above for Example 1, with appropriate changes in monomer amounts as recited in TABLE 2.

Multicomponent Polymeric Particle Characterization

The average particle size of the multicomponent polymeric particles in the latexes of Comparative Example C1 and Examples 1-5 were measured using a Brookhaven BI-90 particle size analyzer available from Brookhaven Instruments Corporation. The results are provided in TABLE 3.

The percent void fraction for the multicomponent polymeric particles in the latexes of Comparative Example C1 and Examples 1-5 was determined by taking a 10 wt % dispersion of the multicomponent polymeric particles in propylene glycol, which was then mixed and poured into a weight-per-gallon cup which was capped and weighed. A 10 wt % water blank was also measured, and the difference in the weight was used to calculate the density of the sample, from which the percent void fraction was calculated. The results are provided in TABLE 3.

TABLE 3

| Multicomponent Particles | Particle size (nm) | Void Fraction (%) |
|---|---|---|
| Comparative Example C1 | 523 | 36 |
| Comparative Example C2[1] | 350 | 25 |
| Example 1 | 551 | 36 |
| Example 2 | 792 | 30 |
| Example 3 | 505 | 34 |
| Example 4 | 647 | 34 |
| Example 5 | 595 | 32 |

[1]SunSpheres ™ SPF Booster available from The Dow Chemical Company

Comparative Example SDC1-SDC2 and Examples SD1-SD5: Spray Drying

Multicomponent polymeric particles prepared according to each of Comparative Example C1-C2 and Examples 1-5 were spray dried according to the following procedure in Comparative Example SDC1-SDC2 and Examples SD1-SD5, respectively. Polyethylene glycol (HallStar® PEG 400-ML esterification product from the reaction of coco-derived fatty acid and polyetylene glycol available from HallStar) (12 wt %) was added into the latex containing the multicomponent polymeric particles as a dust control aid. A two-fluid nozzle atomizer was equipped on a Mobile Minor Spray Dryer (available from GEA Process Engineering Inc.). The spray drying was performed under an inert nitrogen atmosphere. Nitrogen was supplied to the atomizer at ambient temperature and was set at 1 bar with a 50% flow, which provided a 6.0 kg/hour of nitrogen flow rate through the atomizer The multicomponent polymeric particles with polyethylene glycol was fed to the atomizer at a flow rate of 30 mL/min using a peristaltic pump (Masterflex L/S). Heated nitrogen was used to evaporate the water from the latex. The drying gas was nitrogen with an inlet temperature set at 140° C. The outlet temperature was equilibrated at 40 to 50° C. through modulation of the latex feed rate. The resulting spray dried, multicomponent polymeric particle powder was collected in a glass jar attached to the cyclone and vacuum dried at room temperature to remove any residual moisture.

Comparative Examples SC1-SC3 and Examples S1-S5: Sunscreen Formulations

Alcohol based sunscreens were prepared in each of Comparative Examples SC1-SC3 and Examples S1-S5 having the generic formulation noted in TABLE 4.

The Phase A components for each of Comparative Examples SC1-SC3 and Examples S1-S5 were mixed at room temperature with mild agitation until dissolved. The avobenzone, 2-ethylhexyl 2-hydroxybenzoate (Octisalate), octocrylene and oxybenzone were added as UV absorbers. The neopentyl glycol diheptanoate was added as an emollient. Dimethicone was included as a skin conditioner. The acrylate copolymer (e.g., Epitex® AC powder water resistant polymer available from The Dow Chemical Company) was added as a film former. Tocopherol (Vitamin E) was added as an antioxidant and skin conditioner. Then Phase B spray dried, multicomponent polymeric particles prepared according to Comparative Example SDC1-SDC2 and Examples SD1-SD5, as noted in TABLE 5, were added with mild stirring to provide sunscreen formulations. Note that Comparative Example SC3 was a control formulation that did not contain multicomponent polymeric particles.

TABLE 4

| Phase | Ingredient INCI name | Parts by weight (pbW) |
|---|---|---|
| A | SD alcohol 40-B | remainder to 100 pbw total |
| A | avobenzone | 3.00 |
| A | octisalate | 4.50 |
| A | octocrylene | 7.00 |
| A | oxybenzone | 4.00 |
| A | neopentyl glycol diheptanoate | 1.00 |
| A | dimethicone | 0.90 |
| A | Styrene/Acrylates Copolymer[1] | 0.70 |
| A | Tocopherol (Vitamin E) | 0.10 |
| B | spray dried, multicomponent polymeric particles | 4.00 |

[1]Epitex ™ AC powder water resistant polymer available from The Dow Chemical Company.

TABLE 5

| Sunscreen formulation | Spray dried multicomponent polymeric particles |
|---|---|
| SC1 | Comparative Example SDC1 |
| SC2 | Comparative Example SDC2 |
| SC3 | — |
| S1 | Example SD1 |
| S2 | Example SD2 |
| S3 | Example SD3 |
| S4 | Example SD4 |
| S5 | Example SD5 |
| S6 | Example SD6 |

Particle Size Distribution/Dispersibility

The particle size distribution was observed for the spray dried, multicomponent polymer particle powders from Comparative Examples SDC1-SDC2 and Examples SD1-SD5 diluted in ethanol and shaken by hand prior to addition into the test chamber of a Malvern MS-2000 with Mastersizer 2000 software. The primary particle volume % in the particle size distribution having a particle size <1 μm is reported in TABLE 6.

The particle size distribution was also observed for the multicomponent polymer particles in the sunscreen formulations prepared according to Comparative Examples SC1-SC2 and Examples S1-S5. The sunscreen formulations according to Comparative Example SC1-SC2 and Examples S1-S5 were subjected to both a low energy and a medium energy homogenization technique.

The low energy table shaker homogenization technique performed using an Eberbach's Benchtop Fixed Speed Reciprocal Shaker. Test vials containing the sunscreen formulations were subjected to a reciprocal shaking at the low speed setting for two hours prior to addition into the test chamber of a Malvern MS-2000 with Mastersizer 2000 software. The primary particle volume % in the particle size distribution having a particle size <1 μm is reported in TABLE 6.

The medium energy vortex mixer homogenization technique testing was performed using a FlackTek SpeedMixer DAC 150 FV-K. The sunscreen formulations were loaded into a sample cell together with grinding beads (cerium stabilized zirconia with a nominal diameter of 0.5 mm) and vortex mixing at 2,000 rpm for two minutes prior to addition into the test chamber of a Malvern MS-2000 with Mastersizer 2000 software. The primary particle volume % in the particle size distribution having a particle size <1 μm is reported in TABLE 6.

TABLE 6

| Multicomponent polymeric particle powder | Vol % |
|---|---|
| Comparative Example SDC2 | 3.8 |
| Example SD1 | 2.4 |
| Example SD2 | 3.4 |
| Example SD3 | 3.1 |
| Comparative Example SC1 (w/low energy mixing) | 1.4 |
| Comparative Example SC2 (w/low energy mixing) | 14.5 |
| Example S1 (w/low energy mixing) | 2.5 |
| Example S2 (w/low energy mixing) | 7 |
| Example S3 (w/low energy mixing) | 58.1 |
| Example S4 (w/low energy mixing) | 72.7 |
| Example S5 (w/low energy mixing) | 3.6 |
| Example S3 (w/medium energy mixing) | 83.6 |
| Comparative Example SC2 (w/medium energy mixing) | 40.6 |

The particle size distribution for the multicomponent polymer particles in the sunscreen formulations prepared according to Example S3 was retested after aging at room temperature for 20 days. The aged sunscreen formulation was subjected to medium energy mixing prior to addition into the test chamber of a Malvern MS-2000 with Mastersizer 2000 software. The particle size distribution of the aged formulation was observed to be essentially unchanged from that of the unaged formulation.

SPF Boosting Efficacy

The SPF boosting efficacy of the sunscreen formulations prepared according to Comparative Example SC3 and Example S3 were evaluated by measuring the sun protection factor (SPF) of the sunscreen formulations. The sunscreen formulations were spread-coated on a 5 cm×5 cm poly methyl methacrylate (PMMA) plate at a level of 50 mg using finger cots. The SPF was measured using a UV-2000S with an integrating sphere and SPF Operating Software supplied by LabSpheres (North Sutton, N.H., USA). The UV-2000S measures the UV absorbance of a sample over UV radiation wavelengths (290-400 nm) for each sample and calculates an SPF value based on the observed UV absorbance spectrum. In comparison with the control (Comparative Example SC3), the sunscreen formulation of Example S3 containing the SPF boosting, multicomponent polymeric particles of the present invention was observed to exhibit a boost efficacy of about 25% per 1 wt % of added multicomponent polymeric particles.

We claim:
1. A suncare formulation, comprising:
a dermatologically acceptable organic carrier;
a UV radiation absorbing agent;
an SPF booster, wherein the SPF booster comprises a multistage polymeric particle, comprising:
(i) a core, wherein the core comprises, as polymerized units, 20 to 60 wt %, based on weight of the core, of a monoethylenically unsaturated carboxylic acid core monomer; and 40 to 80 wt %, based on weight of the core, of a non-ionic ethylenically unsaturated core monomer;
(ii) an inner shell, wherein the inner shell comprises, as polymerized units, 90 to 99.9 wt %, based on weight of the inner shell, of a non-ionic ethylenically unsaturated inner shell monomer; 0.01 to 9.95 wt %, based on weight of the inner shell, a monoethylenically unsaturated carboxylic acid inner shell monomer; and 0.05 to 9.99 wt %, based on weight of the inner shell, of an aliphatic inner shell monomer selected from the group consisting of allyl acrylate, allyl methacrylate and mixtures thereof;
(iii) an outer shell, wherein the outer shell comprises, as polymerized units, 10 to 45 wt %, based on weight of the outer shell, of a non-ionic ethylenically unsaturated outer shell monomer; 50 to 88.9 wt %, based on weight of the outer shell, of an aliphatic outer shell monomer selected from the group consisting of allyl acrylate, allyl methacrylate and mixtures thereof; 0.1 to 10 wt %, based on weight of the outer shell, of a monoethylenically unsaturated non-carboxylic acid outer shell monomer; and, 1 to 25 wt %, based on weight of the outer shell, of an ethylenically unsaturated surfactant outer shell monomer;
wherein the core, when dry, contains at least one void; and wherein the multistage polymeric particle has an average particle size, when dry, of 50 to 1,000 nm.
2. The suncare formulation of claim 1, further comprising an optional additive.
3. The suncare formulation of claim 2, further comprises a film forming agent.
4. The suncare formulation of claim 3, wherein the film forming agent includes a mixture of a styrene/acrylate copolymer and a silicone polymer and wherein the UV radiation absorbing agent includes a mixture of UV radiation absorbing agents.
5. The suncare formulation of claim 4, wherein the dermatologic ally acceptable organic carrier includes an alcohol selected from the group consisting of at least one of methyl alcohol, ethyl alcohol and isopropanol.
6. The suncare formulation of claim 1, wherein the multistage polymeric particle has an average particle size, when dry, of 500 to 800 nm.
7. The suncare formulation of claim 6, wherein the multistage polymeric particle contains less than 0.001 wt %, based on weight of the multistage polymeric particle, of polymerized units of styrene monomer in the backbone chain of the core, the inner shell and the outer shell combined.
8. The suncare formulation of claim 7, wherein the inner shell includes:
a first inner shell, wherein the first inner shell comprises, as polymerized units, 90 to 99.9 wt %, based on weight of the first inner shell, of a non-ionic ethylenically unsaturated first inner shell monomer; and 0.1 to 10 wt %, based on weight of the first inner shell, a monoethylenically unsaturated carboxylic acid first inner shell monomer; and
a second inner shell, wherein the second inner shell comprises, as polymerized units, 90 to 99.5 wt %, based on weight of the second inner shell, of a non-ionic ethylenically unsaturated second inner shell monomer; and 0.5 to 10 wt %, based on weight of the second inner shell, of an aliphatic second inner shell monomer selected from the group consisting of allyl acrylate, allyl methacrylate and mixtures thereof.
9. The suncare formulation of claim 8, wherein the ethylenically unsaturated surfactant outer shell monomer is selected from the group consisting of an anionic surfactant monomer according to Formula I, a non-ionic surfactant monomer according to Formula II and mixtures thereof;

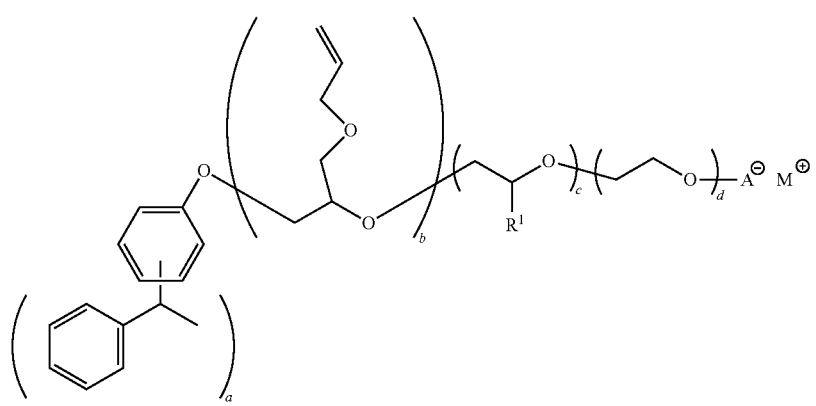
(I)

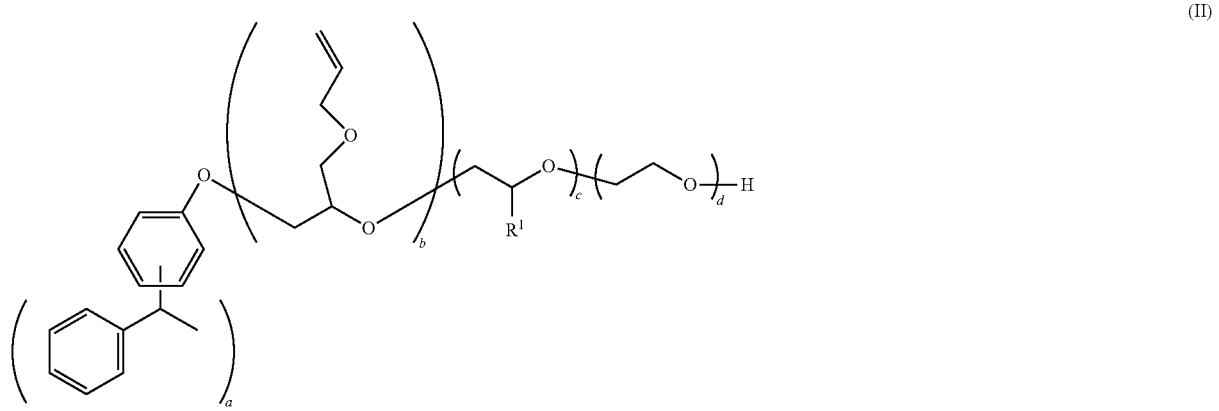
(II)

wherein a is an average of 1-3; wherein b is an average of 1-3; wherein c is an average of 0-5; wherein d is 4-100; wherein A is an anion; and wherein M is a cation charge balancing the anion.

10. The suncare formulation of claim 8, wherein the ethylenically unsaturated surfactant outer shell monomer is an anionic surfactant monomer according to Formula I;

wherein a is an average of 2; wherein b is an average of 2; wherein c is 0; wherein d is an average of 10 to 20; wherein A is $SO_3^-$ and wherein M is $NH_4^\pm$.

\* \* \* \* \*